United States Patent
Grass et al.

(10) Patent No.: US 9,850,531 B2
(45) Date of Patent: Dec. 26, 2017

(54) MOLECULAR CODE SYSTEMS (71) Applicant: ETH ZURICH, Zurich (CH)

(72) Inventors: Robert N. Grass, Zurich (CH); Wendelin Jan Stark, Zurich (CH)

(73) Assignee: ETH Zurich, Zurich (CH)

( * ) Notice: Subject to any disclaimer, the term of this patent is extended or adjusted under 35 U.S.C. 154(b) by 330 days.

(21) Appl. No.: 14/384,852

(22) PCT Filed: Mar. 26, 2013

(86) PCT No.: PCT/CH2013/000052
§ 371 (c)(1),
(2) Date: Sep. 12, 2014

(87) PCT Pub. No.: WO2013/143014
PCT Pub. Date: Oct. 3, 2013

(65) Prior Publication Data
US 2015/0030545 A1 Jan. 29, 2015

(30) Foreign Application Priority Data

Mar. 26, 2012 (EP) .................. 12002096

(51) Int. Cl.
*C12Q 1/68* (2006.01)
*B01L 3/00* (2006.01)
*C40B 20/04* (2006.01)
*C40B 50/16* (2006.01)

(52) U.S. Cl.
CPC .............. *C12Q 1/686* (2013.01); *B01L 3/54* (2013.01); *C12Q 1/68* (2013.01); *B01J 2219/00572* (2013.01); *C40B 20/04* (2013.01); *C40B 50/16* (2013.01)

(58) Field of Classification Search
None
See application file for complete search history.

(56) References Cited

U.S. PATENT DOCUMENTS

| 6,303,290 B1 | 10/2001 | Liu et al. | |
|---|---|---|---|
| 2009/0252811 A1* | 10/2009 | Lin | A61K 9/0019 424/501 |
| 2010/0258743 A1 | 10/2010 | Bortolin | |

(Continued)

FOREIGN PATENT DOCUMENTS

| WO | 2003/030129 A2 | 4/2003 | |
|---|---|---|---|
| WO | WO 2010/006753 A2 * | 1/2010 | .......... A61K 9/0019 |

OTHER PUBLICATIONS

Fujiwara et al, J. Biomed. Res., Part A, pp. 103-112, published online Nov. 15, 2006.*

(Continued)

*Primary Examiner* — Robert T. Crow
(74) *Attorney, Agent, or Firm* — Renner, Otto, Boisselle & Sklar, LLP (57) ABSTRACT

The present invention relates to a method for protecting and recovering nucleic acids. This method may be applied in a verification method of products using molecular code systems or it may be applied in a storage method for nucleic acids. The invention further provides specific particles, their use in secure marking; products suitable for such verification method, to processes for manufacturing such products and methods for reading the information.

5 Claims, 2 Drawing Sheets (56) References Cited

U.S. PATENT DOCUMENTS

2011/0123620 A1* 5/2011 Weigandt ............ A61K 9/0019
                                                        424/484
2012/0045515 A1* 2/2012 Liu ..................... A61K 9/5115
                                                        424/489

OTHER PUBLICATIONS

He et al, J. Am. Chem. Soc., vol. 125, pp. 7168-7169, published on the web May 21, 2003.*
International Search Report for corresponding International Application No. PCT/CH2013/000052 dated Jun. 25, 2013.
Pierre et al., "Encapsulation of deoxyribonucleic acid molecules in silica and hybrid organic-silica gels", Journal of Materials Science: Materials in Medicine 12, 2001, pp. 51-55.
Gill et al., "Bioencapsulation within synthetic polymers (Part 1): sol-gel encapsulated biologicals", Tibtech, Jul. 2000, vol. 18, pp. 282-296.
Gill et al., "Bioencapsulation within synthetic polymers (Part 2): non-sol-gel-protein-polymer biocomposites", Tibtech, Nov. 2000, vol. 18, pp. 469-479.
Shiu et al., :Behavior of single DNA molecules in the well-ordered nanopores, Journal of chromatography A, 1206, 2008, pp. 72-76.
Romanyuk et al., "Light emission from nanocrystalline silicon clusters embedded in silicon dioxide: Role of the suboxide states", Journal of Luminescence, 130, 2010, pp. 87-92.
Oh et al., "Integrated bio-inorganic hybrid systems for nano-forensics", The Royal Society of Chemistry, 40, 2011, pp. 583-595.
Lim et al., "Highly stable, amphiphilic DNA-encoded nanoparticle conjugates for DNA encoding/decoding applications", Journal of Materials Chemistry, 21, 2011, pp. 9467-9470.
Grigsby et al., "Balancing protection and release of DNA: tools to address a bottleneck of non-viral gene delivery", Journal of The Royal Society Interface, 7, Sep. 2009, pp. S67-S82.
Kapusuz et al., "Synthesis of DNA-encapsulated silica elaborated by sol-gel routes", J. Master. Res., vol. 28, No. 2, Jan. 28, 2013, pp. 175-184.
Tom, "Reaction of Natural Rubber with Hydrofluoric Acid", Journal of Polymer Science, vol. XX, 1956, pp. 381-386.
Catania et al., "Determination of 5-Methylcytosine by Acid Hydrolysis of DNA with Hydrofluoric Acid", Analytical Biochemistry, 156, 1987, pp. 347-351.
Kaneko, "Review—Determination of pore size and pore size distribution—1. Absorbents and catalysts", Journal of Membrane Science, 96, 1994, pp. 59-89.
Yu et al., "Impact of Silica Nanoparticle Design on Cellular Toxicity and Hemolytic Activity", ACS Nano, vol. 5, No. 7, 2011, pp. 5717-5728.

* cited by examiner

SEQUENCE LISTING

```
<160> NUMBER OF SEQ ID NOS: 2

<210> SEQ ID NO 1
<211> LENGTH: 17
<212> TYPE: DNA
<213> ORGANISM: Artificial Sequence
<220> FEATURE:
<223> OTHER INFORMATION: Primer

<400> SEQUENCE: 1
gtaaaacgac ggccagt                                                    17

<210> SEQ ID NO 2
<211> LENGTH: 17
<212> TYPE: DNA
<213> ORGANISM: Artificial Sequence
<220> FEATURE:
<223> OTHER INFORMATION: Primer

<400> SEQUENCE: 2
caggaaacag ctatgac                                                    17
```

MOLECULAR CODE SYSTEMS

This application is a national phase of International Application No. PCT/CH2013/000052 filed Mar. 26, 2013 and published in the English language, which claims priority to Application No. EP 12002096.1 filed Mar. 26, 2012.

The present invention relates to a method for protecting and recovering nucleic acids. This method may be applied in a verification method of products using molecular code systems or it may be applied in a storage method for nucleic acids. The invention further relates to specific particles, in particular silica encapsulated DNA particles, and to their use in secure marking. It further relates to an invisible secure marking or information which is a part of such product. The invention further relates to products suitable for such verification method, to processes for manufacturing such products and methods for reading the information.

Forgery, grey market and illegal re-imports are considered an increasing issue in industry. Therefore, many attempts are made for secure marking of products.

Nucleic acids represent the coding language of all life forms, having a nearly unimaginably storage capacity, typical bacterial DNA has a storage capacity of 5,000 terabyte. It is considered advantageous utilizing this coding system to store and send hidden messages, to uniquely tag and verify products. However, nucleic acids are chemically very damageable. Within a living organism this chemical damage (up to 1 million individual molecular lesions per cell and per day) is rapidly repaired by a biological repair system. Outside of the organism there is no repair system and nucleic acid stability is further impaired by the near omnipresence of enzymes accelerating the degradation of nucleic acids. Making use of nucleic acids as a non-biological coding system, therefore requires the protection of nucleic acids from chemical attack.

WO03030129 discloses DNA-containing particles as labels for a product.

Oh et al. (Chem. Soc. Rev, 40, 583-595 (2011)) disclose bio-inorganic hybrid systems for nano-forensics. According to the authors, DNA is protected against environmental conditions by encapsulation in layered double hydroxides (LDHs). These systems are considered disadvantageous, as the materials are liable to acid attack.

Lim et al (J. Mater. Chem., 21, 9467-9470 (2011)) and Grigsby et al (J. R. Soc. Interface, 7, S67-S82 (2010)) disclose protection of DNA utilizing polymers. These systems are considered disadvantageous, as the polymers do not protect the nucleic acids against degradation induced by heating or radical attack.

Liu et al (U.S. Pat. No. 6,303,290) disclose encapsulation of biomaterials in porous glass like matrixes, such as porous silica. These systems are considered disadvantageous, as sensitive to moderate or harsh environmental conditions, such as the presence of radical species, acids or bases, which can diffuse into the porous material and damage the DNA therein. Further, under prolonged immersion in buffers the nucleic acids may be eluted out of the porous material in an uncontrollable way.

Pierre et al (J. of Materials Science, 2001, 51-55) discloses encapsulation of natural DNA (salmon sperm) in hybrid organic-silica gels. According to this disclosure, and supported by the data provided therein, the DNA is encapsulated inside the gel due to a permanent bonding to the gel network. The DNA is not encapsulated within silica particles.

Bartolin (US2010/0258743) relates to the use of nucleic acid labeled tags for location analysis. The document fails to specifically disclose suitable tags, and also to specifically disclose release methods of the DNA encapsulated therein.

Gill et al. (TIBTECH, 2000, vol. 18, 282-296) provides a general overview to the field of bioencapsulation within synthetic polymers.

Shiu (J. of Chromatography, 2008, 72-76) describes the behaviour of single DNA molecules in nanotubes.

Romanyuk et al (J. of Luminescence, 2010, 87-91) describe light emission from nanocrystalline silicon clusters.

Kaupusuz et al. (J. Mater. Res., vol 28, 2013) disclose the synthesis of DNA encapsulated silica by sol-gel routes and functional materials obtained. The DNA of the functional material according to this document, although termed "encapsulated", is immobilized only. As outlined by Kapusuz, the functional materials aim to retain the native structure and reactivity of the DNA.

Thus, it is an object of the present invention to provide a molecular code system that mitigates at least some of these drawbacks.

In its broadest sense, the present invention provides a method for protecting and recovering nucleic acids. The protecting step is achieved by encapsulating nucleic acids with silica to obtain particles; the recovering step is achieved by dissolving these particles in an aqueous fluoride solution, optionally followed by purification steps, to recover the nucleic acid and the information associated therewith. This method of protecting and recovering nucleic acids has a multitude of industrial applications, including verification methods for commercial items and storage methods of naturally occurring nucleic acids.

The present invention will be described in more detail below. It is understood that the various embodiments, preferences and ranges may be combined at will. Further, depending of the specific embodiment, selected definitions, embodiments or ranges may not apply.

Unless otherwise stated, the following definitions shall apply in this specification:

The term "nucleic acid" is known in the field and includes DNA and RNA. Nucleic acids include both, naturally occurring nucleic acids and artificial nucleic acids ("analogues").

The term "silica" is known as the chemical compound $SiO_2$ in both its crystalline and amorphous state. The term "silica" also includes amorphous glass matrices. Suitable glass matrices have a $SiO_2$ content of at least 70 wt %. Glass matrices consequently may include other elements (particularly selected from the group consisting of carbon, sodium, calcium, boron, lead, phosphorous and aluminum) and/or other compounds.

"Hydrofluoric Acid" is a known chemical compound which is very aggressive. For example, it is toxic by inhalation, in contact with skin and if swallowed, it causes severe burns. It is also corrosive to many materials, including leather, rubber and many organics. Tom (Journal of Polymer Science, 1956, p. 381-86) describes the reaction of natural rubber with hydrofluoric acid. Catania et al (Analytical Chemistry, 1987, 347-351) describes hydrolysis of DNA by hydrofluoric acid. Dissolving Hydrofluoric acid is known to produce an aqueous fluoride solution. It is also known that such solutions may be buffered by adding fluoride salts.

The term "particle" describes solid spheres with a primary diameter between 10 and 10000 nm, preferably 100 and 1000 nm. The term "particle" also includes larger particles which are composed of aggregates of primary particles with diameters between 10 and 10000 nm. The particle size may be determined by measuring the specific surface areas (e.g. by the BET method).

The term "non-porous" is known in the field. It is accepted that the term "non-porous", and in this context also the term "encapsulated" have a context specific meaning. In the context of the present invention, the term particularly describes a specific property of the particles disclosed herein, namely particles with a minimum pore volume of relevant pores. Pores are considered relevant (i) if they are of the "open" type, i.e. pores are accessible from (or in communication with) the particles external surface; (ii) if they are of the "intraparticle" type, i.e. located in a particle and not between particles; and (iii) if they are of the "meso" size, i.e. approximately 2-50 nm in diameter. Such pores are described in Kaneko, particularly table 1, which is incorporated by reference (J. Membrane Sci. 1994, 96, 59-89). Advantageously, non-porous particles show a pore volume of relevant pores (i.e. pores of the open, intraparticle type and meso size) below 0.1 $cm^3/g$, preferably below 0.01 $cm^3/g$. The relevant pore volume may be determined by nitrogen adsorption and utilization of the Barrett-Joyner-Halenda method for mesopores (Yu T et al. ACS Nano 2011, 5(7), 5717-5728), subtracting contributions from interparticle pores (Kaneko, see above). The non-porous nature of the particles described herein prevents diffusion of small molecules (e.g. hydroxyl radicals) to the interior of the particle, thereby protecting the nucleic acid core and/or prevents the diffusion of nucleic acids out of the particle's core, thereby maintaining the information associated with said particle. This may also be assessed by a stability test using Copper salts, $H_2O_2$ and sodium ascorbate; particles with the pores defined herein are stable over a period of more than 30 min.

The term "matrix" describes a continuous phase in either liquid or solid (crystalline and/or amorphous) state.

The term "product" is used in its broadest sense and includes commercial items, such as pharmaceutical products, food products and polymer based products.

The term "verification method" describes a method that allows distinguishing and/or identifying products. Thus, verification methods are suitable (i) for distinguishing genuine products from false articles (ii) for identification of products (e.g. by batch type, manufacturing site, manufacturing time).

The term "storage method" describes a method that allows retaining and recovering materials and information associated therewith over a prolonged period of time and/or under adverse environmental conditions. Thus, storage methods are suitable (i) for conserving nucleic acids and the information encoded therein and (ii) for maintaining DNA databases. The term DNA database, as used herein, relates to a well organized collection of samples, each consisting of a multitude of particles encapsulating DNA. Such DNA databases are known per se, but not using the core-shell particles of the present invention.

The term "bar code system" is known and particularly describes a collection of defined sequences of characters (such as letters, numbers or nucleobases) known to the proprietor of the bar code system. These sequences of characters may be mixed with random sequences of characters to encrypt the defined sequence. According to the present invention, nucleobases are used as characters for the bar code system.

The figures attached to this specification are intended to further illustrate the invention.

FIG. 1 provides and schematic overview of the verification method as described herein. Free nucleic acids may be analyzed using RT-PCR (1). Free nucleic acids do not withstand environmental conditions, such elevated temperatures or as OH radicals (2), and are thus unsuited as a product barcode in commodity products. DNA encapsulated in silica (3) withstands harsh environmental conditions (4) and may be incorporated in a product. It can be separated from the product extracted from the protecting silica particle by treatment with fluoride ions (5). The thus recovered, and optionally purified, DNA may be analysed using RT-PCR (6).

FIG. 3 provides sketch of silica encapsulation chemistry (not to scale), which was employed in example 7:1. Silica is surface modified with APTES to carry amine groups (positive charge). 2. DNA adsorbs readily on the positively charged spheres. 3. APTES is used to give the thus obtained surface silica affinity. 4. A closed (non-porous) and thicker silica layer is then grown onto the pre-silanized surface.

FIG. 4 provides a TEM image of material produced according to ex. 7. The inner silica core (indicated with white dotted line) is coated with DNA (can not be seen on TEM), which is then protected by an outer silica layer.

In a first aspect, the invention relates to a verification method for a product, said product comprising a matrix and particles, wherein said particles comprise a nucleic acid core and a silica coating, wherein said method comprises the step of dissolving said particles in an aqueous fluoride solution. This aspect of the invention shall be explained in further detail below:

Verification Method:

The inventive method is based on the concept that a specific and known nucleic acid (e.g. a DNA fragment) is encapsulated in silica particles. These particles are added to the product which is to be verified (e.g. polymer matrix of a product or coating of a tablet). After manufacturing, the product is distributed and used as usual. If the manufacturer, or another authorized person, wishes to verify this product, the above particles are isolated (separated) from the product (e.g. oxidation, dissolution of the matrix). In a further step, the above particles are dissolved to extract the previously encapsulated nucleic acid. The obtained mixture may be purified by purification strategies (e.g. magnetic extraction, dialysis). The thus obtained nucleic acid is analysed using known analytical methods for nucleic acid identification and quantification (e.g. PCR). The data set obtained is than compared with the original data set to verify the product.

Figure 5:
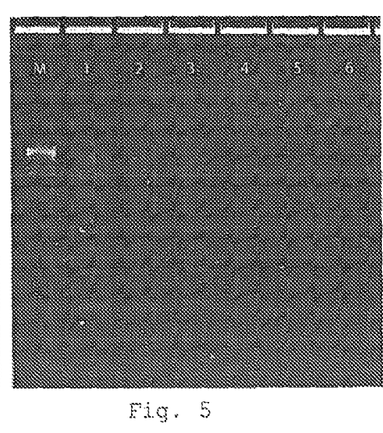
FIG. 5 provides an Agarose plate following the electrophoresis of samples prepared in example 8 (Lane 1-3 for 10, 20 and 30 minutes) and example 9 (Lane 4-6 for 10, 20 and 30 minutes). While the unprotected DNA (example 9, Lane 4-6) was completely degraded during the radical stress experiment, the DNA protected within the silica spheres (example 8, lane 1-3) was hardly affected. Lane M contains an untreated reference DNA ladder plus.

Consequently, in one advantageous embodiment, the invention relates to a verification method as described herein, wherein said method comprises the steps of (a) isolating said particles from said product; (b) dissolving the thus obtained particles in an aqueous fluoride solution; (c) separating and optionally purifying the thus obtained nucleic acid; (d) analyzing the thus obtained nucleic acid; (e) comparing the thus obtained data set with at least one predefined data set. To simulate the influence of environmental conditions on encapsulated nucleic acids, a stress test was preformed (FIG. 5). In this test, the most aggressive radical oxygen species were generated in solution and exposed to native DNA and DNA containing particles as described herein. Native DNA was destroyed by the radical oxygen species within just a few seconds, as confirmed by gel-electrophoresis. The DNA containing particles were stable and undamaged for at least 30 min, as confirmed by gel-electrophoresis (after treating the particles with aqueous buffered fluoride solution). This shows the capacity of the particles as described herein to successfully protect nucleic acids from extremely harsh environmental conditions.

Product:

The inventive method may be applied to any product compatible with silica. Silica is a very inert material and due to its beneficial properties already present in many products. Consequently, the invention relates to a verification method as described herein, wherein said product is selected from the group consisting of (i) food products, (ii) pharmaceutical products, (iii) polymer based products (such as bulk materials of polymers, paints, dyes).

Matrix:

Due to its inert properties, silica may be combined with almost any other material. Consequently, the invention relates to a verification method as described herein, wherein said product comprises a matrix of solid, semi-solid or liquid material.

Particles:

As outlined above, the particles comprise a nucleic acid core and a silica coating.

The coating comprises or consists of silica, preferably non-porous silica. The thickness of this coating may vary over a broad range, but typically is within 10 and 500 nm. Advantageously, porosity and thickness of the coating are adapted to prevent, or substantially prevent, diffusion of reactive species, such as hydroxy radicals, to the particle's core and to prevent, or substantially prevent, the diffusion of nucleic acids out of the particle's core.

The core comprises or consists of one or more nucleic acids. In a preferred embodiment, the core comprises (i) one or more positively charged solid spheres, such as silica spheres modified with amino groups; (ii) one or more nucleic acids adsorbed on these spheres; and (iii) optionally aminoalkyl substituted alkoxysilanes adsorbed on these nucleic acids. Suitable nucleic acids, such as DNA, comprise 10-500 base pairs.

The inclusion of nucleic acids into amorphous silica particles enables an optimal protection of nucleic acids against all environmental conditions outside living organisms. This hybrid material can be utilized to store and send hidden messages, uniquely tag products and merchandise and as an invisible "ink" to identify marked objects. This technology allows the unique tagging of products and thus enables fraud protection and anti-counterfeiting. Nearly any product could be uniquely tagged with a nucleic acid code. Using only two 20 basepair sequences (primers) a total of $10^{20}$ individual codes can be generated which further permits product retraceability and facilitate liability control.

Figure 3:
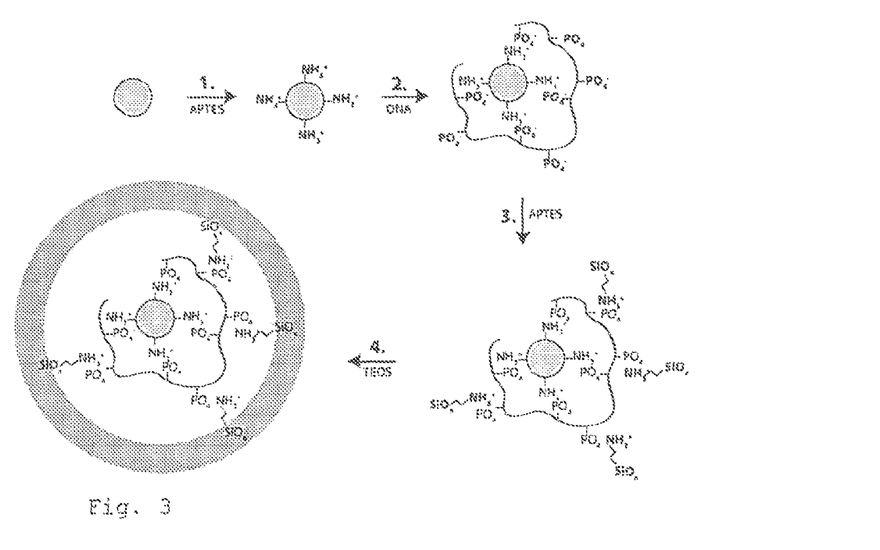

Such particles are, in principle, known and/or obtainable according to known methods. In one embodiment, commercial silica spheres (monodisperse ~200 nm) are surface modified with APTES (amino propyl tri-ethoxysilane, FIG. 3, step 1), rendering an amine (—$NH_2$) surface functionality. This surface functionality gives these silica spheres a positive charge. These spheres are combined with a solution comprising nucleic acids, which are strongly negatively charged due to the phosphate groups on the backbone. The nucleic acids adsorb strongly on the surface of the modified silica spheres (FIG. 3, step 2). The now negative surface functionality (free phosphate groups from the nucleic acids) are again bound to APTES, now resulting in an SiOx surface functionality (very thin, monolayer, FIG. 3, step 3). This functionality is then utilized to grow a thicker $SiO_2$ coating ontop of the nucleic acids with Tetra ethoxy silane (TEOS) and base in ethanol (FIG. 3, step 4) to obtain the above core-shell particles. The thus obtained particles are particularly suitable in methods that involve protecting and recovering nucleic acids, particularly in the verification and storage methods described herein. The invention also relates to core-shell particles obtainable by or obtained by methods as described herein.

In a further advantageous embodiment, said step a (isolating said particles from said product) may be performed by melting the product or by dissolving the product in a suitable solvent and separating the particles from the solution by e.g. centrifugation, filtration, magnetic separation. Due to the stability of the core-shell particles, this step is not temperature sensitive and may be performed at temperatures exceeding 150° C. The choice of solvents strongly depends on the material of the product. Suitable solvents may be readily identified by a person skilled in the art and include organic solvents as well as aqueous (acidic or basic) solvents.

In a further advantageous embodiment, said step b (dissolving the thus obtained particles in an aqueous fluoride solution) is performed at 0-50° C. in the presence of an aqueous fluoride solution. In an advantageous embodiment, said aqueous fluoride solution is an aqueous buffered fluoride solution. Accordingly, the core-shell particles may be dissolved in a buffered oxide etch solution. Such solutions are a standard reagent used for etching silica wafers and typically comprise an aqueous mixture of ammonium fluoride and hydrofluoric acid. Step b may be performed at temperatures between 0-50° C., typically at room temperature. In this step, the particles are dissolved within several seconds resulting in free nucleic acids within a high-salt solution ($F^-$, $NH_4^+$, $SiF_6^{2-}$). Surprisingly, and in contrast to the teaching of Catania et al (discussed above), nucleic acids remain unchanged during this step. Without being bound to theory, it is believed the nucleic acids are not attacked or destroyed during this step due to the buffered nature and/or the relatively high pka of hydrofluoric acid.

In a further advantageous embodiment, said step c, (separating and optionally purifying the thus obtained nucleic acid) may be done by way of drop dialysis or nucleic acid extraction. In order to purify the nucleic acids obtained in step b, known methods and known reagents/kits may be used. Suitable methods include (i) drop dialysis (e.g. on a Millipore filter) and (ii) nucleic acid extraction (e.g. using a standard Qiagen Kit), using solid phase reversible immobilization magnetic beads, using ion exchange resins, solid phase nucleic acid extraction techniques as well as liquid phase nucleic acid extraction techniques (e.g. Phenol/Chloroform method)).

In a further advantageous embodiment, said step d (analyzing the thus obtained nucleic acid) may be done by known methods. Known methods for analyzing the purified nucleic acids of step c include nucleic acid amplification reactions (such as polymerase chain-reaction (PCR), real-time polymerase chain reaction (RT-PCR), ligase-chain reactions (LCR), transcription mediated amplification (TMA), nucleic acid sequence based amplification (NASBA)), DNA microarrays, hybridization probes (e.g. TaqMan®, LNA®, Molecular Beacon, Scorpion®), gel-electrophoresis and nucleic acid specific dyes (e.g. Hoechst 33258, Hoechst 33342, SYBR Green, Ethidium bromide) as well as suitable combinations of these methods. All methods proved that pure and unmodified nucleic acids are obtained after protecting ("encapsulating") and recovering ("steps a-c"). In a preferred embodiment, step d may be done by way of RT-PCR or gel-electrophoresis.

In a further advantageous embodiment, said step e (comparing the thus obtained data set with at least one predefined data set) may be done manually or by the aid of a computer program. Depending on the set up of the verification method and the analysis step, the comparison between the obtained data set (sequence) and the predefined data set may be done manually or by a computer program.

In a further embodiment, the invention relates to the use of particles as defined herein in a verification method, particularly in a verification method as described herein.

In a further advantageous embodiment, the invention also relates to a bar-code system comprising core-shell particles as described herein and to the use of core-shell particles as described herein as a bar-code system. With this system, products can be easily und uniquely tagged and authenticated. This bar-code system is highly cryptographic by design and can not be retro-engineered. Nucleic acid bar code systems are at least equivalent to a digital 64 bit key, i.e. ~$10^{20}$ possibilities and are, therefore, ideal as an invisible anti-counterfeiting tag. As discussed above, in order to utilize nucleic acids as anti-counterfeiting bar-code systems, these sensitive chemical compounds have to be protected from environmental attack during the product lifetime. Optimal protection of nucleic acids in the environment, however, strongly conflicts with barcode read-out utilizing standard nucleic acid analysis tools. To overcome this problem, core-shell particles as described herein are provided. These particles enable both (i) an optimal protection of nucleic acids from environmental attack and (ii) the release of the encapsulated nucleic acids upon a chemical trigger: aqueous fluoride solution. Dissolution of silica using fluoric acids is a known process in chip manufacturing. This process enables an efficient bar-code read-out. It was surprisingly found that nucleic acids are stable in the presence of hydrofluoric acid. Usually strong acids rapidly destroy nucleic acids and therefore an un-packing step utilizing hydrofluoric acid does not seem feasible. The utilization of a buffered oxide etch solution solves this problem and results in an excellent nucleic acid stability during the un-packing step. Further, it was surprisingly found that nucleic acid purification steps (e.g. using Roche Kit, SPR1 technology and dialysis) in the presence of hydrofluoric acid comprising solutions is feasible. Such purification is beneficial when the nucleic acids are to be analyzed with RT-PCR technology after the un-packing step.

Figure 4:
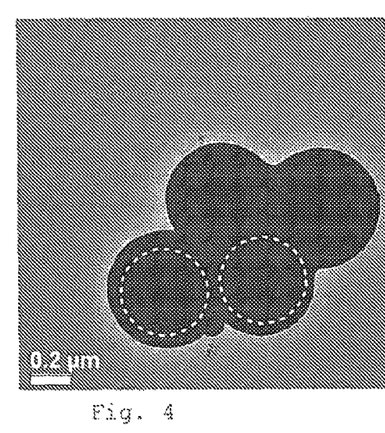

In a second aspect, the invention relates to a product comprising a matrix and particles, wherein (a) said matrix contains (i.e. comprises or consists of) a polymeric material and (b) said particles contain a nucleic acid core and a non-porous silica coating. This aspect of the invention shall be explained in further detail below:

Particles:

Generally, encapsulation of nucleic acids with silica utilizing sol-gel technology and adapted methods is known and described e.g. in U.S. Pat. No. 6,303,290. Advantageously, particles are used as described in the first aspect of the invention. Suitable are in particular particles as shown in FIG. 3 and FIG. 4 and/or obtainable according to the example 2. The amount of particles in said product may vary over a broad range. Due to the advanced analysis of nucleic acids, the concentration may be very low, such as 1 ppb to 1 ppm.

Matrix:

As outlined above, a wide variety of polymer materials are suitable, including both, natural and synthetic polymer materials. In an advantageous embodiment, said matrix is selected from the group consisting of thermoplastics, silicones and rubbers. Suitable thermoplastics include polyethylene, poly-propylene, polyvinyl chloride, polyepoxide, poly-tetrafluoroethylene, aramide, polyester (such as SU8), polyurethane, polylactic acid, poly-3-hydroxybutyrate, polyethylene terephthalate, polybutylene terephthalate, polystyrene, polycarbonate, polyamide, polyacrylate, poly (methyl methacrylate), polysulfone, polyoxymethylene, polyethersulfone, polyphenylsulfone, polyether ether ketone (PEEK), basic methacrylate copolymer (BMC, Poly (butyl methacrylate-co-(2-dimethylaminoethyl) methacrylate-co-methylmethacrylate), Eudragit®), poly-benzimidazole, ethylene chlorotrifluoroethylene, poly-dimethylsiloxane, polyamide-imide, poly(p-phenylene sulfide), polyvinylidene difluoride.

Suitable rubbers include natural or synthetic rubbers.

In an advantageous embodiment, the polymer is selected from the group of polyamides.

In a further advantageous embodiment, the polymer is selected from the group consisting of polyethylene terephthalate and polybutylene terephthalate.

In a further advantageous embodiment, the polymer is selected from the group of acrylonitrile-butadiene-styrene-copolymers.

Products:

As outlined above, a wide variety of products are suitable. This includes bulk materials of polymers; paints and dyes; packaging material; pharmaceuticals; food products, personal ornaments.

In one embodiment, the product referred to above is a bulk material of a polymer. Typically, polymers are produced and distributed as bulk material, such as pellets or granules. These bulk materials may contain the particles referred to above. It is thus possible to verify the bulk material as well as final products (such as sports shoes, handbags, luxury goods) made thereof. Such bulk materials of polymers are therefore useful for e.g. batch-numbering, for internal use of the manufacturer, for external use with the processing industry, for product protection. The invention thus also provides for polymers as described above, particularly in the form of pellets or granules, comprising particles as described above.

In one further embodiment, the product referred to above is a paint or a dye. Typically, paints and dyes are produced and distributed as bulk material. These bulk materials may contain the particles referred to above. It is thus possible to verify the bulk material as well as final products (such as a car body) made thereof. Such paints and dyes are therefore useful for e.g. batch-numbering, for internal use of the manufacturer, for external use with the processing industry, for product protection. The invention thus also provides for paints and dyes as described above, comprising particles as described above.

In one further embodiment, the product referred to above is a packaging material, such as a container, cardboard material, a bottle. These packaging materials may contain the particles referred to above. Such packaging materials are therefore useful for e.g. batch-numbering, for internal use of the manufacturer, for external use with distributors, for product protection. The invention thus also provides for packaging materials, comprising particles as described above.

In one further embodiment, the product referred to above is a pharmaceutical, such as a solid, semi-solid or liquid pharmaceutical composition. Particularly suited are solid dosage forms, such as coated tablets, uncoated tablets. These dosage forms may contain the particles referred to above. Such pharmaceuticals are therefore useful for e.g. batch-numbering, for internal use of the manufacturer, for external use with distributors, for product protection, for compliance. The invention thus also provides for pharmaceutical compositions, comprising particles as described above.

In one further embodiment, the product referred to above is a food product. As silica is inert towards human administration, it is possible to directly include the particles described above into the food. Due to its outstanding stability, a read-out of the bar code is possible after food processing, such as cooking, heating in a microwave oven or backing. Such food products are therefore useful for e.g. batch-numbering, for internal use of the manufacturer, for external use with distributors, for food protection. The invention thus also provides for food products, comprising particles as described above.

In one further embodiment, the product referred to above is a personal ornament, such as a talisman, amulet, ring or the like. Such ornaments typically contain one or more natural or synthetic gemstone(s)/jewel(s). These gemstones may be coated with the particles as described herein to contain specific information. Accordingly, the present invention relates to the encapsulation of genomic DNA in a 3D object, such as a gemstone/jewel.

In a further embodiment, the invention provides for the use of particles as described herein for labelling a product as herein.

In a further embodiment, the invention provides for the use of particles as described herein for labelling a polymer, particularly selected from the group consisting of polyamides, PET, PBT and ABS.

In a third aspect, the invention relates to Process for manufacturing a product as described herein comprising the steps of (a) coating a matrix as described herein with a composition comprising said particles or (b) incorporating a composition comprising said particles in said matrix. This aspect of the invention shall be explained in further detail below:

As outlined above, the nucleic acids encapsulated in silica particles as described herein do not distinguish from conventional silica particles in terms of physical characteristics and handling. Thus, any known manufacturing process that comprises a coating step or an incorporation of silica is also compatible with the core-shell particles described herein. Particularly, the present core-shell particles are stable under aqueous (basic or acidic) conditions, in organic solvents, at manufacturing temperatures (exceeding 150° C.), under high pressure/shear stress. Thus, conventional extrusion processes, spraying processes, coating processes, melting processes may be used. It is considered a clear advantage that the manufacturer or a commercial item does not need to adapt its manufacturing process, the core-shell particles described herein may be simply added at any process step convenient.

In one embodiment, the invention provides for manufacturing a product as described herein comprising the steps of coating a matrix as described herein (i) with a composition which consists of said particles optionally diluted with a diluent or (ii) with a composition which consists of said particles and conventional silica particles optionally diluted in a diluent. Thus, the coating with the core-shell particles may be a separate manufacturing step or may be integrated in an existing manufacturing step, simply by combining the present core-shell particles with conventional silica particles. This process may be applied to coated tablets.

In a further embodiment, the invention provides for manufacturing a product as described herein comprising the steps (i) incorporating a composition consisting of said particles optionally diluted with a diluent or (ii) incorporating a composition which consists of said particles and conventional silica particles optionally diluted in a diluent. Thus, the incorporating with the core-shell particles may be a separate manufacturing step or may be integrated in an existing manufacturing step, simply by combining the present core-shell particles with conventional silica particles. In a next step, the matrix material containing the inventive particles is further processes by known technology—such as hot pressing, extrusion, injection molding, solvent casting—to obtain the desired product.

This process may be applied to products containing polymer materials, such as sports shoes.

This process may also be applied to obtain personal ornaments.

In a further embodiment, the invention relates to a product obtainable by or obtained by a process as described herein.

In a forth aspect, the invention relates to a storage method for nucleic acids, comprising the step of (a) providing particles comprising a nucleic acid core and a silica coating (b) storing the thus obtained particles and (c) dissolving said particles in an aqueous fluoride solution which is optionally buffered. This aspect of the invention shall be explained in further detail below:

By the above storage method, the integrity of nucleic acids is improved when compared to known methods of storing nucleic acids. Particularly, hydrolysis and oxidation of nucleic acids is prevented. The storage method is thus particularly suitable for long-term storage, such as 1 month, preferably 1 year or preferably more than 10 years.

Step (a): Particles are obtained as described above, i.e. by encapsulating nucleic acids with silica. In a preferred embodiment, the nucleic acids are naturally occurring nucleic acids, including chromosomes and genes. Thus, the genetic instructions required for development and functioning of a specific living organism may be stored by the above method. This enables set-up of a gene database. The present invention therefore also provides (i) for a gene database using the above storage method and (ii) for using the above storage method for running a gene database.

Step (b): In a preferred embodiment, storing of the encapsulated nucleic acid takes place at temperatures between −18° C. to +35° C., preferably 0° C.-25° C., much preferably at room temperature. Thus, the inventive storage method may be performed without external cooling of the samples to be stored. This is considered an significant advantage over conventional storage methods for nucleic acids, which typically require cooling, often in liquid nitrogen.

Humidity and pressure are less relevant parameters for storing; for ease of handling, ambient conditions are preferred.

Step (c): To recover the stored nucleic acid, the protocol of the first aspect of the invention may be followed. Thus, to recover the stored nucleic acid, the particles stored in step (b) are dissolved in an aqueous fluoride solution and further optionally purifying the thus obtained nucleic acid. Advantageously, the fluoride solution is buffered.

The above storage method may be used to maintain a DNA/RNA data base. Thus, the invention also relates to a data base of nucleic acids comprising a multitude of core shell particles as described herein, characterized in that particles are spatially separated according to the nucleic acids comprised in their core. Such data base may be used to preserve genetic information of living organisms, such as of endangered species.

The following examples are intended to further illustrate the invention without limiting it.

Example 1: Preparation of Silica Core (FIG. 3, Step 1)

Silica core particles are prepared by adding 4.8 g of TEOS (tetraethoxysilane) to a mixture of 10.8 g ammonia solution (25 wt % $NH_3$), 10.8 g water and 58.3 g ethanol. The resulting solution was stirred for three days after which the white precipitate that had formed was centrifuged and the pellet was redispersed in 100 ml ethanol. To this dispersion 4 ml of APTES were added. After 4 hours the precipitate was centrifuged and the pellet washed twice in ethanol and once in water (re-dispersing the pellet and centrifuging each time) and stored in 20 ml of ethanol. The resulting amine functionalized silica particles had a particle size (from SEM) of 300 (+−50) nm and were present at a concentration of 60 mg/ml.

Example 2: Preparation of Silica Coated DNA Containing Particles (FIG. 3, Steps 2, 3 and 4)

5 µl of a double stranded DNA fragment (bluescript 238 BP, 28 ng/µl) were mixed with the 10 µl of amine functionalized silica particles (Example 1), 500 µl TE buffer (10 mM Tris-HCl, 1 mM EDTA, pH=8), and 5 µl DNA ladder plus (Invitrogen). The resulting solution was centrifuged (21500 g) for 1 minute, the supernatant discharged and the pellet was dispersed in 1 ml of ethanol.

To this solution 2 µl APTES were added together with 20 µl TEOS and 20 µl TE Buffer. After leaving the solution to react over night at room temperature in a shaker, the solution was centrifuged for 5 minutes. The supernatant was discharged, and the precipitate washed once with 1 ml ethanol and once with 1 ml TE buffer (centrifuging for 1 minute each time) and dispersed in 100 µl of TE Buffer.

Figure 1:
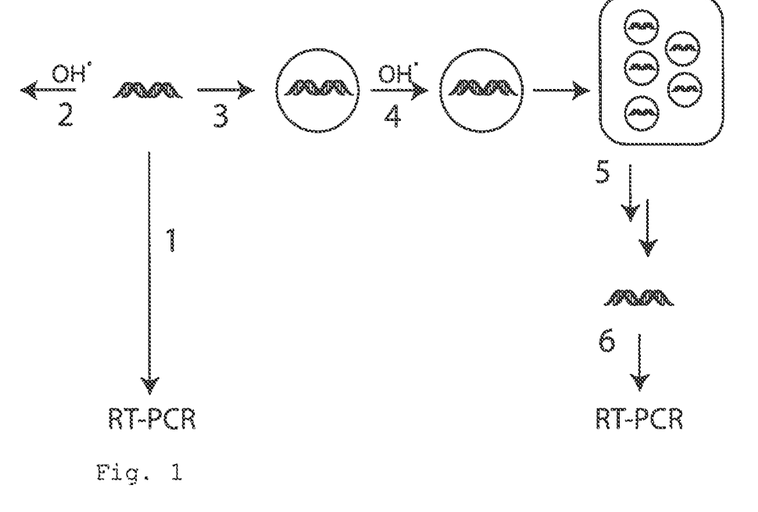
Figure 2:
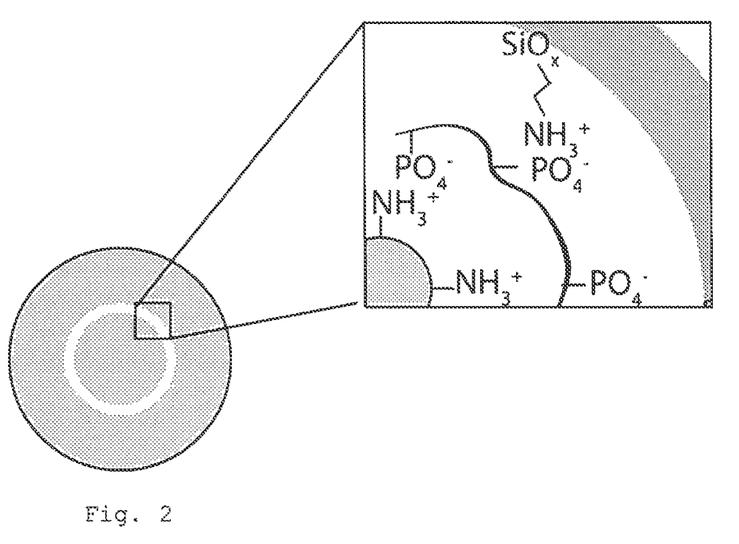
FIG. 2 provides a schematic drawing of the particles suitable for the verification method and may be obtained according to example 7. Negatively charged DNA is packed in between a silica core and a silica shell. The negative charges of the phosphate group of DNA are compensated by the amine groups of APTES.

Example 3: Dissolution of Silica Coated DNA Containing Particles (FIG. 2, Step 5)

5 µl oft the turbid material produced in example 2 was added to 10 µl of a buffered oxide etch solution (BOE, 0.34 g $NH_4F$+10 g HF (1%)) and shaken for 1 minute. The resulting clear solution was dropped onto a dialysis filter (Millipore 0.025 µm VSWP) and dialysed against 10 ml of pure water for 30 minutes. Following dialysis the sample was ready for analysis via real-time polymerase chain reaction (RT-PCR).

Analysis of Recovered DNA Sample: (FIG. 2, step 6)

1 µl oft the dissolved and dialyzed sample was added to 10 µl of RT-PCR master mix (Roche, Lightcycler 480 SYBR Green I Master Mix), 7 µl of PCR grade water (Roche) and 2 µl Primer mix (GTA AAA CGA CGG CCA GT and CAG GAA ACA GCT ATG AC, 5 µM each). RT-PCR was performed utilizing a MJ Research DNA Engine Opticon with 40 cycles (15 s@95° C.; 30 s@56° C.; 30 s @72° C.) and the evolution of the fluorescence of the sample was followed. Following the RT-DNA amplification the melting curve of the DNA was measured by heating the DNA from 60° C. to 93° C., stopping at each 0.5° C. for 10 seconds and measuring the sample fluorescence.

The sample produced required 8.2 cycles to reach a fluorescence threshold value of 0.01, and a DNA melting temperature of 86.5° C. The positive control (1 µl of DNA fragment @1 ng/µl) required 5 cycles (melting temp. 86° C.) to reach this threshold value and the negative control (no DNA) required>30 cycles, see Table 1.

Example 4: Control Experiment 1

1 µl of the spheres prepared as described in example 2 were analyzed via RT-PCR without dissolving the silica spheres in the buffered oxide etch. In this case >30 PCR cycles were required to reach the threshold of 0.01 and the melting temperature of the sample was 72° C. (Table 1) This shows the absence of DNA on the surface of the silica spheres and that the DNA present within the sphere can not be detected by enzymes (e.g. taq-polymerase).

Example 5

The material produced in example 2 was diluted 1:10, 1:100, 1:1,000 and 1:10,000 in TE Buffer. 5 µl of each dilution were mixed with 10 µl of BOE solution, mixed and dialyzed against pure water for 30 minutes. RT-PCR of the dialyzed sample was performed as above. Results (Table 1) are reported as cycle number required for a fluorescence threshold of 0.01 together with the melting point of the synthesized DNA.

TABLE 1

| Sample | Dilution (—) | Cycle Nr. | Melting point (° C.) |
| --- | --- | --- | --- |
| Example 3 | None | 8.2 | 86 |
| Ex. 3 pos. control | None | 5.1 | 86 |
| Ex. 3 neg. control | None | >30 | 85.5 |
| Example 4 | None | >30 | 73 |
| Example 5 | 1:10 | 11.6 | 86.5 |
| Example 5 | 1:100 | 16.3 | 86 |
| Example 5 | 1:1000 | 19.1 | 86 |
| Example 5 | 1:10000 | 23.2 | 85.5 |

Example 6: Incorporation into Polymer, Temperature Treatment (FIG. 3, Steps 4, 4', 5 and 6)

10 µl of the material produced in example 2 was let to dry in a glass vial. 1,000 µl of a polymer solution of polysulfone (10 wt %, SolvayPlastics, Udel®, P-1700) in chloroform was added to the vial, which was then thoroughly mixed and sonicated for one minute in an ultrasonic bath. The polymer solution was first let to dry for 10 minutes and then the solvent was extracted in vacuum. The resulting polymer (100 mg) was transparent and no indication of the particles was visible by the naked eye. 10 mg of the polymer were each treated at RT, at 100° C. and at 150° C. respectively for 30 minutes. Following the heat treatment the polymeric samples were each dissolved in 1 ml of dichloromethane and centrifuged 3 times, each time discarding the supernatant and adding 1 ml of dichloromethane to the (invisible) precipitate. Following the last centrifugation step, the supernatant was removed and the vial was let to dry. 20 µl of BOE was added to each vial and mixed for 1 minute. The resulting solutions were dialyzed against pure water and RT-PCR was performed as described in example 3. The results in table 2 are represented as cycle number required for a fluorescence threshold of 0.01

TABLE 2

| Sample | Heat treatment | Cycle Nr. | m.p. (° C.) |
|---|---|---|---|
| Ex. 6 | None | 20 | 86 |
| Ex. 6 | 30 min at 100° C. | 23.4 | 86 |
| Ex. 6 | 30 min at 150° C. | 25.3 | 85.5 |

The results show that although some of the nucleic acid is degraded during the heat treatment, the polymer can still be identified utilizing RT-PCR after heat treatments of 150° C.

Example 7: Silica Sphere Encapsulating DNA Ladder

Amine functionalized silica particles (Example 1, 500 µl), 500 µl TE buffer (10 mM Tris-HCl, 1 mM EDTA, pH=8) and 5 µl DNA ladder plus (Invitrogen) were mixed. 100 µl APTES were added to the solution which was then centrifuged (21500 g) for 5 minutes. The supernatant was discharged and the pellet was redispersed in 1 ml ethanol. After a second centrifugation run, the supernatant was discharged and the pellet was redispersed in 500 µl ethanol. To this, 100 µl of TEOS and 100 µl of TE buffer were added. After leaving the solution to react over night at room temperature in a shaker, the solution was centrifuged for 5 minutes. The supernatant was discharged, and the precipitate washed once with 1 ml ethanol and once with 1 ml TE buffer (centrifuging for 1 minute each time) and dispersed in 1 ml of distilled water. A schematic of the final product is shown in FIG. 2, a schematic of the encapsulation procedure is shown in FIG. 3 and a TEM image of the corresponding particles is shown in FIG. 4.

Example 8: Stability of DNA Ladder in Silica Sphere

105 µl of the dispersion prepared in example 7 were mixed to a solution of 15 µl sodium ascorbate in water (20 mM), +15 µl hydrogen peroxide (20 mM) and 15 µl aqueous solution of $CuCl_2$ (500 µM). 10, 20 and 30 minutes after addition of the $CuCl_2$ solution, an aliquot of 10 µl was taken and the DNA concentration therein was measured utilizing an Invitrogen Qubit HS-dsDNA kit. (Table 3) At every time point an additional aliquot of 40 µl of the original mixture was taken and the silica particles therein were dissolved by adding 60 µl buffered oxide etch. To extract the DNA from the solution, 1.5 µg carboxy coated TurboBeads in aqueous solution (50 µl 0.5 M EDTA, pH 8) were added together with 500 µl binding buffer (2.5 M NaCl, 20 wt % PEG 10,000). After mixing for 5 minutes, the magnetic beads, which bind nucleic acids under these conditions, were separated from the solution by an external solid-state magnet (1×1×1 cm, neodymium based magnet). The magnetic beads were washed with 70% ethanol twice (500 µl each) and the nucleic acids were eluted from the surface of the beads in 30 µl TE buffer. After separating the magnetic beads from the solution and discarding them, 20 µl of the solution was loaded onto an agarose plate (Invitrogen E-Gel EX, 2% agarose) and separated by electrophoresis utilizing an Invitrogen E-Gel® i-Base Power system for 10 minutes (program no. 7). At all three time points (10, 20 & 30 minutes) completely sharp DNA bands could be observed on the plate under illumination (using Invitrogen E-Gel Safe Imager; see FIG. 5, lines 1-3 (line M contains untreated DNA-ladder)). This shows that the DNA protected within the silica particles was not degraded by the radical oxygen species formed during the copper catalysed degradation of hydrogen peroxide.

Example 9: (Control Experiment) Stability of Unprotected DNA Ladder

To test the stability of unprotected DNA ladder to the conditions tested in example 8, 10 µl of DNA ladder plus (Invitrogen) were diluted with 1 ml of water. 35 µl of this solution were mixed with 5 µl sodium ascorbate solution (20 mM), 5 µl hydrogen peroxide solution (20 mM) and 5 µl $CuCl_2$ solution (500 µM). The concentration of the DNA following this procedure was measured after 10, 20 and 30 minutes utilizing an Invitrogen HS-dsDNA kit and no remaining DNA could be observed (see Table 3). 20 µl of the solution at every time point were additionally loaded on an agarose plate (together with the 3 solutions from experiment 8) and separated by electrophoresis. Following the electrophoresis (FIG. 5, lines 4-6) no nucleic acids bands could be identified on the gel in these lines. This result is in line with the quantification results and shows that under the given conditions of example 8 and 9 (ascorbate, hydrogen peroxide and copper chloride) unprotected DNA is completely degraded.

TABLE 3

| ex. | DNA | Time of treatment | Concentration of DNA in sample |
|---|---|---|---|
| 8 | SiO2 protected DNA | 10 minutes | 720 ng/ml |
| 8 | SiO2 protected DNA | 20 minutes | 620 ng/ml |
| 8 | SiO2 protected DNA | 30 minutes | 514 ng/ml |
| 9 | Free DNA | 10 minutes | <0.5 ng/ml |
| 9 | Free DNA | 20 minutes | <0.5 ng/ml |
| 9 | Free DNA | 30 minutes | <0.5 ng/ml |

Example 10: Encapsulated DNA

The ammonium functionalization of silica particles (SiO2-R-B1181, micro particles GmbH) was performed by adding 25 µl N-trimethoxylsilylpropyl-N,N,N-trimethylammonium chloride (TMAPS, 50% in MeOH, ABCR GmbH) to 2.5 ml $SiO_2$ particles (50 mg/ml, 147 nm) in isopropanol, stirring for 24 h at room temperature and purification by sedimentation and redispersion in 2.5 ml water.

The DNA amplicon was prepared by annealing the following synthetic sequence with its complementary sequence: ATT CAT GCG ACA GGG GTA AGA CCA TCA GTA GTA GGG ATA GTG CCA AAC CTC ACT CAC CAC TGC CAA TAA GGG GTC CTT ACC TGA AGA ATA AGT GTC AGC CAG TGT AAC CCG AT.

DNA encapsulation: Ammonium functionalized silica particles (35 µl, 50 mg/ml) were mixed with 10 µl double stranded DNA amplicon (1 mg/ml) and 1 ml water. After intense mixing and centrifugation of the particles for 2 minutes at 21,500 g, the supernatant was discarded and the particles were resuspended in 1 ml $H_2O$. Following 2 additional wash cycles, centrifuged particles were dispersed in 0.5 ml water, after which the co-interacting agent (TMAPS, 50% in MeOH, 0.6 µl) was added while stirring at room temperature. Tetraethoxysilane (TEOS, Z 99.0%, Aldrich Chemistry, 0.6 µl) was added to the mixed solution while vigorously stirring and the mixture was allowed to react at room temperature for 4 hours, after which additional 4 µl of TEOS were added. The mixture was left to react under stirred conditions (900 rpm) for 4 days. The resulting suspension was washed by centrifugation with water twice and diluted to a concentration of 36 µg DNA/ml.

Example 11: (Control Experiment) Free DNA

The DNA amplicon was prepared by annealing the following synthetic sequence with its complementary sequence: ATT CAT GCG ACA GGG GTA AGA CCA TCA GTA GTA GGG ATA GTG CCA AAC CTC ACT CAC CAC TGC CAA TAA GGG GTC CTT ACC TGA AGA ATA AGT GTC AGC CAG TGT AAC CCG AT. The amplicon was diluted in water to a concentration of 60 µg DNA/ml.

Example 12: DNA Release and Analysis

For the extraction of the encapsulated DNA, 10 µl of particle suspension of Example 10 was added to 40 µl of a buffered oxide etch solution (BOE=HF/NH$_4$F, 0.34 g NH$_4$F+10 g HF (1% in water)). Prior to analysis by qPCR the solution was diluted 1:10 with water. Example 11 (control experiment) was processed identically.

DNA analysis: A typical PCR run was performed utilizing 10 µl of real-time PCR master mix (Roche, Lightcycler 480 SYBR Green I Master Mix), 7 µl of PCR grade water (Roche) and 2 µl Primer mix (forward and reverse primers, 5 µM each). Real-time PCR was performed utilizing a MJ Research DNA Engine Opticon with 40 cycles (15 s at 95° C., 30 s at 56° C., 30 s at 72° C.). Real-time PCR was quantified using the corresponding amplicons at known concentrations and preparing standards at 1:10, 1:100, 1:1,000, 1:10,000, 1:100,000 and 1:1,000,000 dilution. For real-time PCR the following primers were used:

```
ATT CAT GCG ACA GGG GTA AG
and
ATC GGG TTA CAC TGG CTG AC.
```

Example 13: Temperature Stability

The solutions of Example 10 and Ref Example 11 were heated (pressurized) to temperatures between 100 and 140° C. for 15 minutes. Following the heat treatment the samples were allowed to cool down and the DNA was released from the encapsulates (Example 10) and analyzed as described in Example 12. Results are given in % of initial DNA concentration (=36 µg/ml for Example 10 and 66 µg/ml for Example 11). Results in Table 4.

TABLE 4

| Temperature | DNA remaining following heat treatment of free DNA (%) | DNA remaining following heat treatment of encapsulated DNA (%) |
|---|---|---|
| No treatment | 100 | 100 |
| 100° C. | 66 | 99 |
| 120° C. | 0.37 | 87 |
| 140° C. | 0.0008 | 10 |

Example 14: Radical Stability

5 µl of the corresponding solutions (Encapsulated DNA, Example 10 and Free DNA, Control Example 11) were mixed with 2.5 µl L-ascorbic acid solution (20 mM), 12.5 µl H$_2$O$_2$ solution (20 mM) and 17.5 µl CuCl$_2$ solution (500 µM), for 5, 10 and 20 minutes and stopped by adding 17.5 µl EDTA (100 mM). Following this procedure 20 µl buffered oxide etch were added to dissolve the particles and the mixtures were dialyzed against pure water (dropped onto dialysis filter for 30 min, Millipore 0.025 µm VSWP) to purify the DNA from qPCR inhibiting components (copper, EDTA etc.). For quantification the standards underwent the same procedure (adding quenching EDTA first). Following this procedure the concentration of the DNA was analyzed by qPCR as described in example 12. Results are given in % of initial DNA concentration (=36 µg/ml for Example 10 and 66 µg/ml for Example 11). Results in Table 5.

TABLE 5

| Radical treatment duration | DNA remaining following radical treatment of free DNA (%) | DNA remaining following radical treatment of encapsulated DNA (%) |
|---|---|---|
| No treatment | 100 | 100 |
| 5 min | 0.00086 | 72 |
| 10 min | 5.6E−7 | 69 |
| 20 min | 5.6E−7 | 44 |

Example 15: Sunlight Irradiation Stability

10 µl of the corresponding solutions (Example 10 and Control Example 11) were left to dry over night. Following sunlight irradiation (Newport Sun Simulator, Class A 91195A-1000, AM1.5global, 1000 W/m$^2$, simulating tropical irradiation at noon time) for various times the samples were rewetted with 40 µl buffered oxide etch and quantified as described in Example 12. Results are given in % of initial DNA concentration (=36 µg/ml for Example 10 and 66 µg/ml for Example 11). Results are given in table 6.

TABLE 6

| Sunlight irradiation duration | Remaining DNA following sunlight irradiation of free DNA (%) | Remaining DNA following sunlight irradiation of encapsulated DNA (%) |
|---|---|---|
| No treatment | 100 | 100 |
| 5 min | 71 | 100 |
| 10 min | 57 | 81 |
| 1 hour | 21 | 65 |
| 5 hours | 1.8 | 65 |

Example 16: Encapsulation of Two Types of DNA

A well known amplicon (pBluescript II KS, MCS, 238 bp) was mixed with a standard DNA ladder (Invitrogen DNA ladder Plus). The ratio of pBluescript amplicon to DNA ladder is 1:30 (wt amplicon/wt DNA ladder). The corresponding solution was diluted to a concentration of 1 mg DNA/ml.

DNA encapsulation: Ammonium functionalized silica particles (35 µl, 50 mg/ml, see Example 10) were mixed with 10 µl of the DNA mixture and 1 ml water. After intense mixing and centrifugation of the particles for 2 minutes at 21,500 g, the supernatant was discarded and the particles were re-suspended in 1 ml H$_2$O. Following 2 additional wash cycles, centrifuged particles were dispersed in 0.5 ml water, after which the co-interacting agent (TMAPS, 50% in MeOH, 0.6 μl) was added while stirring at room temperature. Tetraethoxysilane (TEOS, >99.0%, Aldrich Chemistry, 0.6 μl) was added to the mixed solution while vigorously stirring and the mixture was allowed to react at room temperature for 4 hours, after which additional 4 μl of TEOS were added. The mixture was left to react under stirred conditions (900 rpm) for 4 days. The resulting particle suspension was washed by centrifugation with water twice and diluted to a concentration of 17 mg solids/ml.

Example 17: Labeling of PVC

PVC-particle composites were formed by dissolving a low-cost, commercial grade PVC blend (Bedoma AG, red, K-value 70; containing bis(2-ethylhexyl)phthalate as plasticizer as well as epoxidized soybean oil, glyceryl monooleate, Ca—Zn paste and pigments) in tetrahydrofuran (Sigma-Aldrich, puriss. p.a.) at elevated temperatures (60° C.) at which the encapsulated DNA (Example 16) was added (various solid loadings). The solvent was removed by distillation under reduced pressure (Rotavapor R-200, Büchi). PVC-particle (350 ppm solid loading) composites were heated in air to various temperatures in an oven for various times. For analysis polymer (10-20 mg) was dissolved in THF and the encapsulated DNA particles were collected via centrifugation. DNA extraction from the particles and DNA analysis via real-time PCR was performed as described in example 12, replacing the primers with: GTA AAA CGA CGG CCA GT and CAG GAA ACA GCT ATG AC.

The concentration of DNA extracted as a function of solid loading and heating temperature is shown in Table 7:

TABLE 7

| Solid loading (ppm = mg/kg) | Heat treatment | DNA conc. (μg/g polymer) |
|---|---|---|
| 350 | None | 1E-2 |
| 1 | None | 1E-5 |
| 0.1 | None | 1E-6 |
| 350 | 120° C./15 min | 8E-4 |
| 350 | 140° C./15 min | 5E-4 |
| 350 | 160° C./15 min | 2E-4 |
| 350 | 180° C./15 min | 5E-5 |
| 350 | 200° C./15 min | 4E-5 |
| 350 | 65° C./14 days | 9E-3 |
| 350 | 65° C./53 days | 2E-4 |

Example 18: Labeling of PSU

Incorporation of different weight ratios of DNA/$SiO_2$ particles (1750 ppm=parts per million weight per weight) into the PSU matrix (Mn 22,000 g/mol, Udel®, Dolder AG) was performed by using chloroform as solvent (10% PSU). The composites were prepared by ball milling of the PSU solution (5 ml) with corresponding amounts of particles and $ZrO_2$ milling balls (2.5 g) in a Fritsch premium line Pulverisette 7 (2 cycles a 15 min, 15 min pause). Ball milling was required to disperse the particles within the polymer. The polymer solutions were processed to thin films (15 μm thickness) via solvent-casting. 15 mg PSU containing 1,700 ppm (~0.2 wt %) particles were heated to various temperatures for 15 minutes. The polymer chips were dissolved in chloroform and the supernatant was removed after centrifugation. The obtained pellet consisted of DNA/$SiO_2$ particles which could be dissolved with HF/$NH_4F$ and analyzed by concentration measurements and real-time PCR as described in Example 17. Results are given in Table 8.

TABLE 8

| Solid loading (ppm = mg/kg) | Heat treatment | DNA concentration (μg/g polymer) |
|---|---|---|
| 1700 | None | 6E-2 |
| 1700 | 100° C./15 min | 3E-2 |
| 1700 | 110° C./15 min | 2E-2 |
| 1700 | 120° C./15 min | 2E-2 |
| 1700 | 140° C./15 min | 2E-4 |
| 1700 | 195° C./15 min | 4E-6 |

Example 19: Polyamide Labeling 1.7 mg of particles formed under example 10 were washed twice with hexafluoroisopropanol (HFIP) and diluted in 5 ml HFIP. The resulting suspension was air-sprayed (Airbrush, Revell) onto 5 kg polyamide pellets (Grilamid PA 12). For analysis single pellets were randomly selected (ca 10 mg) and dissolved in 2 ml HFIP. Following washing by centrifugation in HFIP (1×1 ml) and water (1×1 ml) the last centrifugation precipitate was dissolved in 10 μl BOE and analyzed as described in example 12. The presence of the DNA could be uniquely identified utilizing PCR in all samples (CT sample+2<CT negative control; CT=cycle threshold 0.01).

Example 20: PVDC Labeling 1.7 mg of particles formed under example 10 were mixed with 1 kg of a PVDC emulsion. Thin films of PVDC were prepared by casting the emulsion on PE support layers. For analysis the films were dipped for 10 seconds in 2 ml THF. Following centrifugation of the resulting solution and consecutive washing of the precipitate in THF (lx 1 ml) and water (1×1 ml) the last centrifugation precipitate was dissolved in 10 μl BOE and analyzed as described in example 12. The presence of the DNA could be uniquely identified utilizing PCR in all samples (CT sample+2<CT neg. control; CT=cycle threshold 0.01).

Example 21: DNA Gem-Stone with Genomic DNA

Genomic DNA was collected by a buccal swab and extracted and amplified with a commercial kit (Genomeplex whole genome amplification from Buccal Swab, Sigma-Aldrich). The resulting DNA was encapsulated in silica spheres as described in example 10. The resulting material (1.7 mg) was mixed with 100 mg of commercial silica spheres (in water, 50 mg/ml; SiO2-R-B1181, micro particles GmbH) and centrifuged at high speed to result in a blue, opalescent pellet. The pellet was dried and infiltrated with a mixture of 10 mg AIBN per ml of methyl methacrylate. The object was heated to 80° C. for 20 min. to initiate the radical polymerization. After 3 hrs the resulting mechanically stable 3-dimensional object had bluish-opalescent optical properties.

The invention claimed is:

1. A product selected from the group consisting of bulk materials of polymers, paints and dyes, packaging materials, pharmaceuticals and food products;

said product comprising a matrix and particles, wherein said matrix comprises polymeric material; and said particles comprise a core and a silica coating encapsulating said core, said silica coating having a pore volume below 0.01 cm$^3$/g of pores of the open, intraparticle type and meso size, said core comprising:
   (i) one or more solid silica spheres modified with amino groups;
   (ii) one or more nucleic acids adsorbed on said one or more silica spheres; and
   (iii) optionally aminoalkyl substituted alkoxysilanes adsorbed on said nucleic acids;

said particles are present in an amount of 1 ppm or less.

2. The product according to claim 1, wherein said matrix is selected from the group consisting of thermoplastics, silicones and rubbers.

3. The product according to claim 1, selected from the group consisting of packaging materials and food products.

4. The product of claim 1, wherein the nucleic acid comprises 10-500 base pairs.

5. A process for manufacturing a product according to claim 1, comprising the steps:
   a. coating said matrix with a composition comprising said particles; or
   b. Incorporating a composition comprising said particles in said matrix.

* * * * *